US008410099B2

(12) United States Patent
Vernhet et al.

(10) Patent No.: US 8,410,099 B2
(45) Date of Patent: Apr. 2, 2013

(54) SUBSTITUTED 1-BENZYL-CINNOLIN-4(1H)-ONE DERIVATIVES, PREPARATION THEREOF, AND THERAPEUTIC USE THEREOF

(75) Inventors: Claude Vernhet, Paris (FR); Elodie Barbagallo, Paris (FR); Murielle Rinaldi-Carmona, Paris (FR); Pascale Roux, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 12/987,351

(22) Filed: Jan. 10, 2011

(65) Prior Publication Data

US 2011/0144115 A1 Jun. 16, 2011

Related U.S. Application Data

(63) Continuation of application No. PCT/FR2009/051362, filed on Jul. 9, 2009.

(30) Foreign Application Priority Data

Jul. 11, 2008 (FR) ...................................... 08 03974

(51) Int. Cl.
*A01N 43/58* (2006.01)
*A61K 31/50* (2006.01)
(52) U.S. Cl. .......................... 514/248; 544/235; 544/237
(58) Field of Classification Search .................. 544/235, 544/237; 514/248
See application file for complete search history.

(56) References Cited

U.S. PATENT DOCUMENTS

| | | | |
|---|---|---|---|
| 4,581,354 A | 4/1986 | Bell et al. | |
| 5,532,237 A | 7/1996 | Gallant et al. | |
| 6,013,648 A | 1/2000 | Rinaldi et al. | |

FOREIGN PATENT DOCUMENTS

| | | |
|---|---|---|
| EP | 0833818 | 10/2001 |
| WO | WO 02/42269 | 5/2002 |
| WO | WO 03/097597 | 11/2003 |

OTHER PUBLICATIONS

Pinedo et al. (2000) McMahon et al (2000).*
Stern, E., et al., Pharmacomodulations around the 4-Oxo-1,4-dihydroquinoline-3-Carboxamides, a Class of Potent CB2-Selective Cannabinoid Receptor Ligands: Consequences in Receptor Affinity and Functionality, J. Med. Chem., (2007), vol. 50, pp. 5471-5484.
Bouaboula, M., et al., A Selective inverse Agonist for Central Cannabinoid Receptor Inhibits Mitogen-Activated Protein Kinase Activation Stimulated by Insulin or Insulin-Like Growth Factor 1 , The journal of Biological Chemistry, vol. 272, No. 35, (1997), pp. 22330-22339.
Howlett, A. C., et al., International Union of Pharmacology. XXVII. Classification of Cannabinoid Receptors, Pharmacological Reviews, (2002), pp. 161-202, vol. 54 No. 2.
Klein, T. W., et al., Cannabinoid Receptors and Immunity, Immunology Today, (1998), vol. 19, No. 8, pp. 373-381.
Matsuda, L. A., et al., Structure of a Cannabinoid Receptor and Functional Expression of the Cloned CDNA, Nature, vol. 346, (1980), pp. 561-564.
Munro, S., et. al., Molecular Characterization of a Peripheral Receptor for Cannabinoids, Nature, vol. 365, (1993), pp. 61-65.
Paton, W. D. M., et al., Pharmacology of Marijuana, Annu. Rev. Pharmacol., (1975), vol. 15, pp. 191-220.
Pertwee, R. G., et al., Cannabinoid Receptors and Pain, Progress in Neurobiology, vol. 63, (2001), pp. 569-611.
Portier, M., et al., SR144526, an Antagonist for the Peripheral Cannabinoid Receptor that Behaves as an Inverse, Agonist, The journal or Pharmacology and Experimental Therapeutics, vol. 288, No. 2, pp. 582-589, Oct. 13, 1997.
Rinaldi-Carmona, M., et al., Characterization of Two Cloned Human CB1 Cannabinoid Receptor Isoforms, The Journal of Pharmacology and Experimental Therapeutics. vol. 278, No. 2, pp. 871-878, (1996).
Rinaldi-Carmona, M., et al., SR 144528, The First Potent and Selective Antagonist of the CB2 Cannabinoid Receptor, J. Pharmacol. Exp. Therap. (1998), vol. 284, No. 2, pp. 644-650.
Cota, D., et al., Endogenous Cannabinoid System as a Modulator of Food Intake, International Journal of Obesity, vol. 27, pp. 289-301, (2003).
International Search Report for WO2010/004215 dated Jan. 14, 2010.

* cited by examiner

*Primary Examiner* — Paul V. Ward
(74) *Attorney, Agent, or Firm* — Jiang Lin

(57) ABSTRACT

The present invention is related to novel substituted 1-benzylcinnolin-4(1H)-one derivatives having affinity for cannabinoid $CB_2$ receptors, their preparation and their therapeutic application.

9 Claims, No Drawings

SUBSTITUTED 1-BENZYL-CINNOLIN-4(1H)-ONE DERIVATIVES, PREPARATION THEREOF, AND THERAPEUTIC USE THEREOF

This application is a Continuation of International Application No. PCT/FR2009/051362, filed Jul. 9, 2009, which is incorporated herein by reference in its entirety.

A subject-matter of the present invention is novel substituted 1-benzylcinnolin-4(1H)-one derivatives having affinity for cannabinoid $CB_2$ receptors, their preparation and their therapeutic application.

$\Delta^9$-THC is the main active constituent extracted from Cannabis sativa [Paton, Annual Review in Pharmacology (1975) 15, 191-220].

Numerous papers have described not only psychotropic effects of cannabinoids but also an influence of the latter on the immune function [Klein et al., Immunology Today (1998) 19, 373-381], the control of pain [Pertwee, Progress in Neurobiology (2001) 63, 569-611], food intake [Cota et al., International Journal of Obesity (2003) 27, 289-301] and many other biological functions [Nahas et al., Marihuana and Medicine (1999), Humana Press: Totowa, N.J., USA].

The effects of cannabinoids are due to interaction with specific high affinity G protein-coupled receptors present at the central and peripheral level [Howlett et al., Pharmacological Reviews (2002) 54, 161-2002].

The central effects of cannabinoids concern a first type of cannabinoid receptor ($CB_1$) present mainly in the brain but also in the periphery [Matsuda et al., Nature (1990) 346, 561-564]. Furthermore, Munro et al. [Nature (1993) 365, 61-65] cloned a second type of cannabinoid receptor referred to as $CB_2$, which is present in the periphery and in particular in the cells of the immune system. In some pathological conditions, the presence of $CB_2$ receptors is observed in the brain.

Some indole derivatives have been cited in the prior art as exhibiting an affinity for $CB_2$ receptors; mention may be made of patent applications U.S. Pat. No. 5,532,237, EP 833 818, U.S. Pat. No. 4,581,354, WO 2002/42269 and WO 2003/097597.

Cinnoline derivatives have been described by E. Stern et al. in J. Med. Chem., 2007, 50, 5471-5484, in particular the compound of formula:

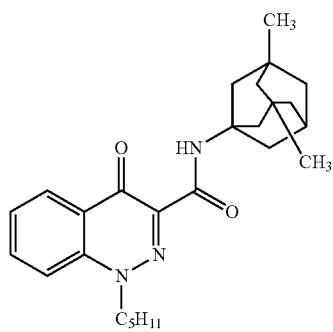

(1)

Novel compounds, which are substituted 1-benzylcinnolin-4(1H)-one derivatives, have now been found which exhibit a high affinity and a high selectivity for cannabinoid $CB_2$ receptors. These compounds have a modulatory effect on the activity of $CB_2$ receptors. Modulatory effect is understood in particular to mean agonist, antagonist and/or inverse agonist effects.

A subject-matter of the present invention is compounds corresponding to the formula (I):

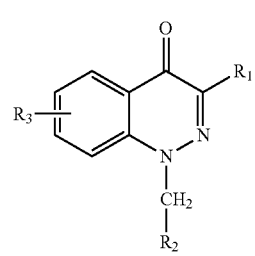

(I)

in which:
R₁ represents:
  a phenyl which is unsubstituted or substituted one or more times by substituents chosen independently from a halogen atom, an Alk group, an OAlk group, a cyano, an —NHSO₂Alk group or an —SO₂Alk group;
  a naphthyl which is unsubstituted or substituted one or more times by substituents chosen independently from a halogen atom, an Alk group or an OAlk group;
  a pyridyl which is unsubstituted or substituted one or more times by substituents chosen independently from a halogen atom, an Alk group or an OAlk group;
  a 1-benzothienyl which is unsubstituted or substituted one or more times by substituents chosen independently from a halogen atom, an Alk group or an OAlk group;
  a 1,3-benzodioxolyl which is unsubstituted or substituted one or more times by substituents chosen independently from a halogen atom, an Alk group or an OAlk group;
R₂ represents:
  an aromatic or heteroaromatic group, the said group being unsubstituted or substituted one or more times by substituents chosen independently from a halogen atom, an Alk group, an OAlk group or a cyano;
R₃ represents a hydrogen atom, a halogen atom, an Alk group or an OAlk group;
Alk represents a ($C_1$-$C_4$)alkyl which is unsubstituted or substituted one or more times by a fluorine atom.

The compounds of formula (I) can comprise one or more asymmetric carbon atoms. They can thus exist in the form of enantiomers or of diastereoisomers. These enantiomers and diastereoisomers, and their mixtures, including racemic mixtures, come within the invention.

The compounds of formula (I) can exist in the form of bases or of addition salts with acids. Such addition salts come within the invention.

These salts are advantageously prepared with pharmaceutically acceptable acids but the salts of other acids of use in the purification or the isolation of the compounds of formula (I) also come within the invention.

($C_1$-$C_4$)Alkyl is understood to mean a linear or branched carbon-comprising radical of 1 to 4 carbon atoms, such as, in particular; methyl, ethyl, propyl, isopropyl, butyl, isobutyl or tert-butyl.

($C_1$-$C_4$)Alkoxy is understood to mean an oxygen atom bonded to a linear or branched carbon-comprising radical of 1 to 4 carbon atoms, such as the methoxy, ethoxy, propoxy, isopropoxy, butoxy, sec-butoxy or tert-butoxy radical.

Halogen atom is understood to mean a fluorine, chlorine, bromine or iodine atom.

Aromatic or heteroaromatic group is understood to mean, for example, a phenyl, naphthyl, pyridyl, thiadiazolyl, indolyl, indazolyl, imidazolyl, benzimidazolyl, benzotriazolyl, benzofuranyl, benzothienyl, benzothiazolyl, benzisothiazolyl, quinolyl, isoquinolyl, benzoxazolyl, benzisoxazolyl, benzoxazinyl, benzodioxinyl, isoxazolyl, benzopyranyl, thiazolyl, thienyl, furyl, pyranyl, chromenyl, isobenzofuranyl, pyrrolyl, pyrazolyl, pyrazinyl, pyrimidinyl, pyridazinyl, indolizinyl, phthalazinyl, quinazolinyl, acridinyl, isothiazolyl, isochromanyl, chromanyl.

According to the present invention, preference is given to the compounds of formula (I) in which:

$R_1$ represents:
- a phenyl which is unsubstituted or substituted once or twice by substituents chosen independently from a halogen atom, an Alk group, an OAlk group or an —$SO_2$Alk group;
- a naphthyl;
- a pyridyl substituted by an Alk group or an OAlk group;
- a 1-benzothienyl;
- a 1,3-benzodioxolyl substituted by one or more fluorine atoms;

$R_2$ represents:
- a phenyl which is unsubstituted or substituted once or twice by substituents chosen independently from a halogen atom, an Alk group or a cyano;
- a thienyl or a pyridyl which is substituted by a halogen atom or an Alk group;

$R_3$ represents a hydrogen or halogen atom or an OAlk group;

Alk represents a ($C_1$-$C_4$)alkyl which is unsubstituted or substituted one or more times by a fluorine atom; in the form of the base or of an addition salt with an acid.

Preference is particularly given to the compounds of formula (I) in which:

$R_1$ represents:
- a phenyl, a 4-chlorophenyl, a 2-fluorophenyl, a 3-fluorophenyl, a 2-methylphenyl, a 4-methylphenyl, a 3-isopropylphenyl, a 2-trifluoromethylphenyl, a 3-trifluoromethylphenyl, a 2-methoxyphenyl, a 4-methoxyphenyl, a 2-trifluoromethoxyphenyl, a 3-trifluoromethoxyphenyl, a 4-trifluoromethoxyphenyl, a 2,3-dichlorophenyl, a 3,5-dichlorophenyl, a 2,3-difluorophenyl, a 2,5-difluorophenyl, a 3-chloro-2-fluorophenyl, a 2-chloro-3-trifluoromethylphenyl, a 3-chloro-5-trifluoromethylphenyl, a 4-chloro-2-trifluoromethylphenyl, a 3-bromo-2-fluorophenyl, a 2-fluoro-3-methylphenyl, a 2-fluoro-4-methylphenyl, a 2-fluoro-3-trifluoromethylphenyl, a 3-fluoro-2-trifluoromethylphenyl, a 3-fluoro-5-trifluoromethylphenyl, a 3-fluoro-2-methoxyphenyl, a 4-fluoro-2-methoxyphenyl, a 2-fluoro-5-trifluoromethoxyphenyl, a 3-isopropyl-6-methoxyphenyl, a 3-(tert-butyl)-6-methoxyphenyl, a 2-(methylsulphonyl)phenyl;
- a naphthyl;
- a 2-methoxypyrid-5-yl, a 2-trifluoromethylpyrid-3-yl;
- a benzothien-2-yl, a benzothien-7-yl;
- a 2,2-difluorobenzodioxol-4-yl;

$R_2$ represents:
- a phenyl, a 4-chlorophenyl, a 2-fluorophenyl, a 4-fluorophenyl, a 2,4-dichlorophenyl, a 2,4-difluorophenyl, a 2-chloro-4-fluorophenyl, a 4-chloro-2-fluorophenyl, a 2-fluoro-4-methylphenyl, a 2-fluoro-4-trifluoromethylphenyl or a 2-fluoro-4-cyanophenyl;
- a 2-chlorothien-5-yl, a 3-trifluoromethylpyrid-6-yl, a 5-chloropyrid-2-yl or a 3,5-difluoropyrid-2-yl;

$R_3$ represents a hydrogen atom, a chlorine atom or a methoxy;

in the form of the base or of an addition salt with an acid.

Mention may in particular be made, among the compounds of formula (I) which are subject-matters of the invention, of the following compounds:

1-(2,4-difluorobenzyl)-3-[2-fluoro-3-(trifluoromethyl)phenyl]-8-methoxycinnolin-4(1H)-one;

3-[2-chloro-3-(trifluoromethyl)phenyl]-1-(2,4-difluorobenzyl)-8-methoxycinnolin-4(1H)-one;

3-[2-chloro-3-(trifluoromethyl)phenyl]-1-(2,4-difluorobenzyl)cinnolin-4(1H)-one;

3-(2,3-dichlorophenyl)-1-(2,4-difluorobenzyl)-8-methoxycinnolin-4(1H)-one;

1-(2,4-difluorobenzyl)-3-[2-fluoro-3-(trifluoromethyl)phenyl]cinnolin-4(1H)-one;

1-(2,4-difluorobenzyl)-3-[3-fluoro-2-(trifluoromethyl)phenyl]cinnolin-4(1H)-one;

1-(4-chloro-2-fluorobenzyl)-3-[2-fluoro-3-(trifluoromethyl)phenyl]cinnolin-4(1H)-one;

1-(2,4-difluorobenzyl)-3-(3-isopropylphenyl)cinnolin-4(1H)-one;

1-(2,4-difluorobenzyl)-3-[3-fluoro-2-(trifluoromethyl)phenyl]-8-methoxycinnolin-4(1H)-one;

1-(2,4-difluorobenzyl)-8-methoxy-3-[3-(trifluoromethoxy)phenyl]cinnolin-4(1H)-one;

4-{[3-(2,3-dichlorophenyl)-4-oxocinnolin-1(4H)-yl]methyl}-3-fluorobenzonitrile;

3-fluoro-4-({3-[2-fluoro-3-(trifluoromethyl)phenyl]-4-oxocinnolin-1(4H)-yl}methyl)benzonitrile;

1-(2,4-difluorobenzyl)-3-(4-fluoro-2-methoxyphenyl)cinnolin-4(1H)-one;

3-(2,3-dichlorophenyl)-1-(2,4-difluorobenzyl)cinnolin-4(1H)-one;

1-(2,4-difluorobenzyl)-3-(5-fluoro-2-methoxyphenyl)cinnolin-4(1H)-one;

1-(2,4-difluorobenzyl)-3-(2-methoxyphenyl)cinnolin-4(1H)-one;

3-(3-bromo-2-fluorophenyl)-1-(2,4-difluorobenzyl)cinnolin-4(1H)-one;

1-(2,4-difluorobenzyl)-3-(2-fluoro-3-methylphenyl)cinnolin-4(1H)-one;

1-(2,4-difluorobenzyl)-3-[2-(trifluoromethyl)phenyl]cinnolin-4(1H)-one;

1-(2,4-difluorobenzyl)-3-[2-(trifluoromethoxy)phenyl]cinnolin-4(1H)-one;

1-(2,4-difluorobenzyl)-3-[3-(trifluoromethoxy)phenyl]cinnolin-4(1H)-one;

1-(2-chloro-4-fluorobenzyl)-3-[2-fluoro-3-(trifluoromethyl)phenyl]cinnolin-4(1H)-one;

1-(4-chloro-2-fluorobenzyl)-3-(5-fluoro-2-methoxyphenyl)cinnolin-4(1H)-one;

3-(3-chloro-2-fluorophenyl)-1-(2,4-difluorobenzyl)cinnolin-4(1H)-one;

3-fluoro-4-({4-oxo-3-[2-(trifluoromethyl)phenyl]cinnolin-1(4H)-yl}methyl)benzonitrile;

1-(2,4-difluorobenzyl)-3-(4-methylphenyl)cinnolin-4(1H)-one;

1-(2,4-difluorobenzyl)-3-[3-(trifluoromethyl)phenyl]cinnolin-4(1H)-one;

1-[(5-chlorothien-2-yl)methyl]-3-[2-fluoro-3-(trifluoromethyl)phenyl]cinnolin-4(1H)-one;

1-(2,4-difluorobenzyl)-3-[2-(trifluoromethyl)pyridin-3-yl]cinnolin-4(1H)-one;

3-(1-benzothien-7-yl)-1-(2,4-difluorobenzyl)cinnolin-4 (1H)-one;
1-benzyl-3-(3-isopropylphenyl)cinnolin-4(1H)-one;
1-(2,4-difluorobenzyl)-3-(5-isopropyl-2-methoxyphenyl) cinnolin-4(1H)-one;
1-(2,4-difluorobenzyl)-3-(1-naphthyl)cinnolin-4(1H)-one;
1-(2,4-difluorobenzyl)-3-[2-(trifluoromethyl)pyridin-3-yl] cinnolin-4(1H)-one;
1-(2,4-difluorobenzyl)-3-[2-fluoro-5-(trifluoromethoxy) phenyl]cinnolin-4(1H)-one;
1-(2,4-difluorobenzyl)-3-(4-methoxyphenyl)cinnolin-4 (1H)-one;
3-(2,2-difluoro-1,3-benzodioxol-4-yl)-1-(2,4-difluorobenzyl)cinnolin-4(1H)-one;
3-(4-chlorophenyl)-1-(2,4-difluorobenzyl)cinnolin-4(1H)-one;
1-[(5-chlorothien-2-yl)methyl]-3-(2,3-dichlorophenyl)cinnolin-4(1H)-one;
1-(4-chloro-2-fluorobenzyl)-3-[3-(trifluoromethyl)phenyl] cinnolin-4(1H)-one;
1-(4-fluorobenzyl)-3-(5-fluoro-2-methoxyphenyl)cinnolin-4(1H)-one;
1-(2-fluoro-4-methylbenzyl)-3-[2-fluoro-3-(trifluoromethyl)phenyl]cinnolin-4(1H)-one;
1-(2-fluorobenzyl)-3-(5-fluoro-2-methoxyphenyl)cinnolin-4(1H)-one;
1-(2,4-difluorobenzyl)-3-(2-fluoro-4-methylphenyl)cinnolin-4(1H)-one;
1-(4-fluorobenzyl)-3-[3-(trifluoromethyl)phenyl]cinnolin-4(1H)-one;
1-(2,4-difluorobenzyl)-3-(3-fluorophenyl)cinnolin-4(1H)-one;
3-(5-fluoro-2-methoxyphenyl)-1-[2-fluoro-4-(trifluoromethyl)benzyl]cinnolin-4(1H)-one;
1-(4-fluorobenzyl)-3-[2-fluoro-3-(trifluoromethyl)phenyl] cinnolin-4(1H)-one;
3-(5-fluoro-2-methoxyphenyl)-1-(2-fluoro-4-methylbenzyl) cinnolin-4(1H)-one;
1-(2-chloro-4-fluorobenzyl)-3-(5-fluoro-2-methoxyphenyl) cinnolin-4(1H)-one;
1-(2,4-difluorobenzyl)-3-(2,5-difluorophenyl)cinnolin-4 (1H)-one;
1-(2,4-difluorobenzyl)-3-[3-fluoro-5-(trifluoromethyl)phenyl]cinnolin-4(1H)-one;
1-(2,4-difluorobenzyl)-3-(2-methylphenyl)cinnolin-4(1H)-one;
1-(2,4-difluorobenzyl)-3-(2-naphthyl)cinnolin-4(1H)-one;
1-(2,4-difluorobenzyl)-3-(2,3-difluorophenyl)cinnolin-4 (1H)-one;
1-[2-fluoro-4-(trifluoromethyl)benzyl]-3-[2-fluoro-3-(trifluoromethyl)phenyl]cinnolin-4(1H)-one;
3-[3-chloro-5-(trifluoromethyl)phenyl]-1-(2,4-difluorobenzyl)cinnolin-4(1H)-one;
3-(3,5-dichlorophenyl)-1-(2,4-difluorobenzyl)cinnolin-4 (1H)-one;
1-(2,4-difluorobenzyl)-3-(2-fluorophenyl)cinnolin-4(1H)-one;
1-(2,4-dichlorobenzyl)-3-(5-fluoro-2-methoxyphenyl)cinnolin-4(1H)-one;
3-[2-fluoro-3-(trifluoromethyl)phenyl]-1-{[5-(trifluoromethyl)pyridin-2-yl]methyl}cinnolin-4(1H)-one;
3-(5-(tert-butyl)-2-methoxyphenyl)-1-(2,4-difluorobenzyl) cinnolin-4(1H)-one;
1-[2-fluoro-4-(trifluoromethyl)benzyl]-3-[3-(trifluoromethyl)phenyl]cinnolin-4(1H)-one;
3-[4-chloro-2-(trifluoromethyl)phenyl]-1-(2,4-difluorobenzyl)cinnolin-4(1H)-one;
1-(2,4-difluorobenzyl)-3-(5-fluoro-2-hydroxyphenyl)cinnolin-4(1H)-one;
1-(2,4-difluorobenzyl)-3-phenylcinnolin-4(1H)-one;
1-(2,4-dichlorobenzyl)-3-[3-(trifluoromethyl)phenyl]cinnolin-4(1H)-one;
1-(2-chloro-4-fluorobenzyl)-3-[3-(trifluoromethyl)phenyl] cinnolin-4(1H)-one;
1-(2-fluoro-4-methylbenzyl)-3-[3-(trifluoromethyl)phenyl] cinnolin-4(1H)-one;
3-(1-benzothien-2-yl)-1-(4-chlorobenzyl)cinnolin-4(1H)-one;
1-(2-fluorobenzyl)-3-[2-fluoro-3-(trifluoromethyl)phenyl] cinnolin-4(1H)-one;
1-[(5-chlorothien-2-yl)methyl]-3-(5-fluoro-2-methoxyphenyl)cinnolin-4(1H)-one;
1-(2,4-difluorobenzyl)-3-[4-(trifluoromethoxy)phenyl]cinnolin-4(1H)-one;
1-(2,4-difluorobenzyl)-3-(6-methoxypyridin-3-yl)cinnolin-4(1H)-one;
3-(2,3-dichlorophenyl)-1-{[5-(trifluoromethyl)pyridin-2-yl] methyl}cinnolin-4(1H)-one;
7-chloro-1-(2,4-difluorobenzyl)-3-[2-fluoro-3-(trifluoromethyl)phenyl]cinnolin-4(1H)-one;
1-(2,4-difluorobenzyl)-3-[3-fluoro-2-(trifluoromethyl)phenyl]-7-methoxycinnolin-4(1H)-one;
7-chloro-3-[2-chloro-3-(trifluoromethyl)phenyl]-1-(2,4-difluorobenzyl)cinnolin-4(1H)-one;
1-(2,4-difluorobenzyl)-7-methoxy-3-[3-(trifluoromethoxy) phenyl]cinnolin-4(1H)-one;
4-({3-[2-chloro-3-(trifluoromethyl)phenyl]-4-oxocinnolin-1 (4H)-yl}methyl)-3-fluorobenzonitrile;
7-chloro-1-(2,4-difluorobenzyl)-3-[3-fluoro-2-(trifluoromethyl)phenyl]cinnolin-4(1H)-one;
7-chloro-3-(2,3-dichlorophenyl)-1-(2,4-difluorobenzyl)cinnolin-4(1H)-one;
7-chloro-1-(2,4-difluorobenzyl)-3-[3-(trifluoromethoxy) phenyl]cinnolin-4(1H)-one;
7-chloro-1-(2,4-difluorobenzyl)-3-[2-(methylsulphonyl) phenyl]cinnolin-4(1H)-one;
1-[(5-chloropyridin-2-yl)methyl]-3-[2-fluoro-3-(trifluoromethyl)phenyl]cinnolin-4(1H)-one;
6-chloro-3-[2-chloro-3-(trifluoromethyl)phenyl]-1-(2,4-difluorobenzyl)cinnolin-4(1H)-one;
6-chloro-1-(2,4-difluorobenzyl)-3-[2-fluoro-3-(trifluoromethyl)phenyl]cinnolin-4(1H)-one;
1-(2,4-difluorobenzyl)-3-[2-fluoro-3-(trifluoromethyl)phenyl]-6-methoxycinnolin-4(1H)-one;
6-chloro-1-[(3,5-difluoropyridin-2-yl)methyl]-3-[2-fluoro-3-(trifluoromethyl)phenyl]cinnolin-4(1H)-one;
in the form of the base or of an addition salt with an acid.

In that which follows, protective group PG is understood to mean a group which makes it possible, on the one hand, to protect a reactive functional group, such as a hydroxyl or an amine, during a synthesis and, on the other hand, to regenerate the reactive functional group intact at the end of the synthesis. Examples of protective groups and protection and deprotection methods are given in "Protective Groups in Organic Synthesis", Green et al., 4th Edition (John Wiley & Sons Inc., New York), 2007.

Leaving group is understood to mean, in that which follows, a group which can be easily cleaved from a molecule by splitting a heterolytic bond with departure of an electron pair. This group can thus easily be replaced by another group during a substitution reaction, for example. Such leaving groups are, for example, halogens or an activated hydroxyl group, such as a methanesulphonate, benzenesulphonate, p-toluenesulphonate, triflate, acetate, and the like. Examples of leaving groups and references for their preparation are given in "Advanced Organic Chemistry", M. B. Smith and J. March, 6th edition, Wiley Interscience, 2007, pp. 496-501.

In accordance with the invention, the compounds of formula (I) can be prepared according to a process which is characterized in that:

a compound of formula:

(II)

in which $R_2$ and $R_3$ are as defined for a compound of formula (I), is reacted in the presence of a base with a compound of formula:

$R_1$—B(OH)$_2$ (III)

in which $R_1$ is as defined for a compound of formula (I).

The reaction is carried out in the presence of a palladium catalyst, such as, for example, tetrakis(triphenylphosphine) palladium, in the presence of a base, such as, for example, sodium carbonate, in a solvent, such as, for example, toluene, methanol or a mixture of these two solvents, at a temperature of between ambient temperature and 100° C.

Optionally, the compound of formula (I) is converted to one of its addition salts with inorganic or organic acids.

The compounds of formula (I) thus obtained can subsequently be separated from the reaction medium and purified according to conventional methods, for example by crystallization or chromatography.

The compounds of formula (I) thus obtained are isolated in the free base or salt form, according to conventional techniques.

The compounds of formula (II) are prepared by reaction of a compound of formula:

(IV)

in which $R_3$ is as defined for a compound of formula (I), with a compound of formula:

Hal-CH$_2$—$R_2$ (V)

in which $R_2$ is as defined for a compound of formula (I) and Hal represents a halogen atom.

The reaction is carried out in the presence of a strong base, such as, for example, sodium hydride, in a solvent, such as, for example, N,N-dimethylformamide, at a temperature of between 0° C. and the reflux temperature of the solvent.

The compounds of formula (III) are commercially available, known or prepared according to methods known to a person skilled in the art.

The compounds of formula (IV) are prepared from a compound of formula:

(VI)

in which $R_3$ is as defined for a compound of formula (I), by reaction with bromine in the presence of a base, such as, for example, potassium ethoxide, in a solvent, such as, for example, acetic acid, at a temperature of between ambient temperature and the reflux temperature of the solvent.

The compounds of formula (V) are commercially available, known or prepared according to methods known to the person skilled in the art.

The compounds of formula (VI) are prepared by cyclization of a compound of formula:

(VII)

in which $R_3$ is as defined for a compound of formula (I), in the presence of sodium nitrite, in a solvent, such as, for example, hydrochloric acid, at a temperature of between 0° C. and ambient temperature.

The compounds of formula (VII) in which $R_3$ is as defined for a compound of formula (I) are prepared according to Scheme I below.

SCHEME I

In stage a1 of Scheme I, the reaction of a compound of formula (VIII) with sulphonyl chloride is carried out at a temperature of between ambient temperature and 100° C.

In stage b1, the compound of formula (IX) thus obtained is reacted with diethyl malonate in the presence of magnesium in a solvent, such as, for example, an ether (for example diethyl ether), at a temperature of between ambient temperature and the reflux temperature of the solvent.

The compound (X) thus obtained is reduced in stage c1 in the presence of zinc and acetic acid in a solvent, such as, for example, tetrahydrofuran, at a temperature of between 0° C. and ambient temperature.

The compound of formula (VIII) is commercially available, known or prepared according to methods known to a person skilled in the art.

According to an alternative form of this process, it is also possible to prepare a compound of formula (VII) in which $R_3$ is as defined for a compound of formula (I) according to Scheme II.

SCHEME II

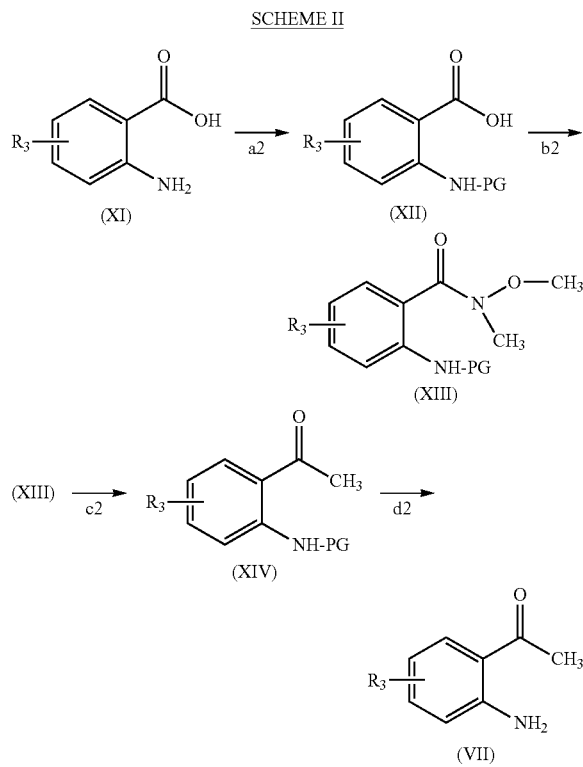

In stage a2 of Scheme II, the amine of the compound of formula (XI) is protected according to methods known to a person skilled in the art.

In stage b2, the compound of formula (XII) thus obtained is reacted with N-methoxymethanamine in the presence of a coupling agent used in peptide chemistry, such as, for example, 1,3-dicyclohexylcarbodiimide (DCC) or (benzotriazol-1-yloxy)tris(dimethylamino)phosphonium hexafluorophosphate (BOP) or (benzotriazol-1-yloxy)tripyrrolidinophosphonium hexafluorophosphate (PyBOP) or 2-(1H-benzotriazol-1-yl)-1,1,3,3-tetramethyluronium tetrafluoroborate, in the presence of a base, such as, for example, triethylamine, N,N-diisopropylethylamine or 4-dimethylaminopyridine, in a solvent, such as, for example, dichloromethane, dichloroethane, N—N-dimethylformamide or tetrahydrofuran, at a temperature of between −10° C. and the reflux temperature of the solvent.

The compound (XIII) thus obtained is reacted in stage c2 with an organometallic compound, such as, for example, methylmagnesium bromide, in a solvent, such as, for example, an ether (for example tetrahydrofuran or dioxane) at a temperature of between −100° C. and ambient temperature.

The compound (XIV) thus obtained is deprotected in stage d2.

The following Examples describe the preparation of some compounds in accordance with the invention. These examples are not limiting and serve only to illustrate the present invention. The numbers of the compounds in the examples refer to what is given in Table I below, in which the chemical structures and the physical properties of a few compounds according to the invention are illustrated.

The following abbreviations are used in the Preparations and in the Examples:
ether: diethyl ether
iso ether: diisopropyl ether
DMSO: dimethyl sulphoxide
DMF: N,N-dimethylformamide
THF: tetrahydrofuran
MeOH: methanol
DCM: dichloromethane
AcOEt: ethyl acetate
HBr: hydrobromic acid
AcONa: sodium acetate
DIPEA: diisopropylethylamine
TFA: trifluoroacetic acid
M.p.: melting point
AT: ambient temperature
HPLC: high performance liquid chromatography The proton nuclear magnetic resonance ($^1$H NMR) spectra are recorded at 200 MHz in $d_6$-DMSO. The chemical shifts δ are expressed in parts per million (ppm). Use is made of the following abbreviations in interpreting the spectra: s: singlet, d: doublet, t: triplet, q: quartet, m: unresolved peak, mt: multiplet, bs: broad singlet, sd: split doublet.

The mixtures of solvents are quantified as ratios by volume.

The compounds according to the invention are analysed by coupled LC/UV/MS (Liquid Chromatography/UV detection/Mass spectrometry). The molecular peak (MH$^+$) and the retention time (rt) in minutes are measured.

The conditions used are as follows:
Conditions A
Column: Symmetry $C_{18}$ (2.1×50 mm) 3.5 μm;
Eluent: A: $H_2O$+0.005% TFA pH≈3;
 B: acetonitrile/0.005% TFA;
Gradient:

| Time (min) | % A | % B |
|---|---|---|
| 0 | 100 | 0 |
| 10 | 10 | 90 |
| 15 | 10 | 90 |
| 16 | 0 | 100 |
| 20 | 0 | 100 |

Flow rate: 0.4 ml/minute;
UV detection: λ=210-220 nm.
Conditions B
An XTerra MS $O_{18}$ (2.1×50 mm) 3.5 μm column is used;
Eluent: A: 10 mM $AcONH_4$ pH≈7;
 B: acetonitrile;
Gradient:

| Time (min) | % A | % B |
|---|---|---|
| 0 | 100 | 0 |
| 10 | 10 | 90 |
| 15 | 10 | 90 |

-continued

| Time (min) | % A | % B |
|---|---|---|
| 16 | 100 | 0 |
| 20 | 100 | 0 |

Flow rate: 0.4 mu/minute;
UV detection: λ=220 nm.
Conditions C
An Acquity BEH $O_{18}$ (2.1×50 mm) 1.7 µm column is used;
Eluent: A: $H_2O$+0.05% TFA pH≈3; acetonitrile (97/3)
   B: acetonitrile/0.035% TFA;
Gradient:

| Time (min) | % A | % B |
|---|---|---|
| 0 | 100 | 0 |
| 2.3 | 5 | 95 |
| 2.9 | 5 | 95 |
| 3 | 100 | 0 |
| 3.5 | 100 | 0 |

Flow rate: 1 ml/minute;
UV detection: λ=220 nm.
Conditions D
A Kromasil $O_{18}$ (2×50 mm) 3.5 µm column is used;
Eluent: A: $H_2O$+0.05% TFA;
   B: acetonitrile/0.035% TFA;
Gradient:

| Time (min) | % A | % B |
|---|---|---|
| 0 | 95 | 5 |
| 6 | 0 | 100 |
| 8 | 0 | 100 |
| 8.1 | 95 | 0 |

Flow rate: 0.7 ml/minute;
UV detection: λ=220 nm.

The mass spectra are recorded in positive electrospray (ESI) mode in order to observe the ions resulting from the protonation of the compounds analysed ($MH^+$) or from the formation of adducts with other cations, such as $N^+$, $K^+$, and the like.

PREPARATIONS

1. Preparations of the Compounds of Formula (VII)

Preparation 1.1

1-(2-Amino-3-methoxyphenyl)ethanone $R_3$=3-OMe.                                                    (VII)

A—3-Methoxy-2-nitrobenzoyl chloride

A mixture of 10 g of 3-methoxy-2-nitrobenzoic acid in 60 ml of thionyl chloride is heated at 75° C. for 3 hours. The reaction mixture is concentrated under vacuum and 10.9 g of the expected compound are obtained, which product is used as is in the following stage.

B—1-(3-Methoxy-2-nitrophenyl)ethanone

A solution of 2 ml of diethyl malonate in 1 ml of EtOH is added, dropwise and at AT, to a mixture of 3.2 g of magnesium in 10 ml of ether and then the mixture is heated to reflux. A solution of 18 ml of diethyl malonate in 10 ml of EtOH is subsequently added dropwise, a solution of 10.9 g of the compound from the preceding stage in 40 ml of ether is then added dropwise and the mixture is heated at reflux for 18 hours. The reaction mixture is run into 100 ml of ether and insoluble material is filtered off. The insoluble material is taken up in a saturated $NH_4Cl$ solution, extraction is carried out with 100 ml of chloroform, the aqueous phase is acidified by addition of 20 ml of a 10% HCl solution, the aqueous phase is reextracted with 100 ml of chloroform, the combined organic phases are dried over $MgSO_4$ and the solvents are evaporated under vacuum. The residue is taken up in a mixture of 10 ml of acetic acid, 1.5 ml of $H_2SO_4$ and 7 ml of water and then heated at reflux for 5 hours. The acetic acid is concentrated under vacuum, the reaction mixture is taken up in 100 ml of water, the aqueous phase is basified by addition of $NH_4OH$, extraction is carried out with 100 ml of chloroform, the organic phase is washed with a saturated NaCl solution and dried over $MgSO_4$ and the solvent is evaporated under vacuum. The residue is chromatographed on silica gel, elution being carried out with the gradient of the cyclohexane/AcOEt mixture from 80/20 (v/v) to 20/80 (v/v). 3.3 g of the expected compound are obtained.

C—1-(2-Amino-3-methoxyphenyl)ethanone

A solution of 3.3 g of the compound from the preceding stage in 100 ml of THF is cooled to 0° C., 13.27 g of zinc and 15 ml of acetic acid are added, the mixture is then left stirring while allowing the temperature to rise to AT and is left stirring at AT for 4 hours. The reaction mixture is filtered through Célite® and the filtrate is concentrated under vacuum. The residue is extracted with THF, the organic phase is washed with 100 ml of a 10% NaOH solution and with a saturated NaCl solution and dried over $MgSO_4$, and the solvent is evaporated under vacuum. The residue is chromatographed on silica gel, elution being carried out with the gradient of the cyclohexane/AcOEt mixture from 80/20 (v/v) to 60/40 (v/v). 2 g of the expected compound are obtained.

Preparation 1.2

1-(2-Amino-4-chlorophenyl)ethanone $R_3$=4—Cl.                                                     (VII)

A—2-[(tent-Butoxycarbonyl)amino]-4-chlorobenzoic acid 19.5 ml of triethylamine are added to a mixture of 10 g of 2-amino-4-chlorobenzoic acid in 45 ml of dioxane and 15 ml of water, a solution of 14 g of di(tert-butyl)dicarbonate in 30 ml of dioxane is then added dropwise and the mixture is left stirring at AT for 48 hours. The reaction mixture is concentrated under vacuum, the residue is taken up in a water/AcOEt mixture, the layers are separated by settling, the organic phase is washed with a saturated NaCl solution and dried over $MgSO_4$ and the solvent is evaporated under vacuum. The residue is chromatographed on silica gel, elution being carried out with the gradient of the AcOEt/cyclohexane mixture. 5.35 g of the expected compound are obtained.

B—tert-Butyl [5-chloro-2-[methoxy(methyl)carbamoyl]phenyl]carbamate 8.78 ml of triethylamine and then 2.11 g of N-methoxymethanamine and 11.27 g of PyBOP are added to a solution of 5.35 g of the compound from the preceding stage in 200 ml of DCM and the mixture is left stirring at AT overnight. The reaction mixture is washed with water, with a 10% NaOH solution and with a saturated NaCl solution and dried over MgSO$_4$, and the solvent is evaporated under vacuum. The residue is chromatographed on silica gel, elution being carried out with the gradient of the cyclohexane/AcOEt mixture from 80/20 (v/v) to 60/40 (v/v). 5.7 g of the expected compound are obtained.

C—tert-Butyl (2-acetyl-5-chlorophenyl)carbamate

A solution of 5.7 g of the compound from the preceding stage in 445 ml of THF is cooled to −40° C., 38.8 ml of methylmagnesium bromide are added dropwise and the mixture is left stirring at AT overnight. The reaction mixture is run onto a 10% HCl solution, extraction is carried out with AcOEt, the organic phase is washed with a saturated NaCl solution and dried over MgSO$_4$, and the solvent is evaporated under vacuum. The residue is chromatographed on silica gel, elution being carried out with the cyclohexane/AcOEt mixture (80/20; v/v) and then with AcOEt. 2.05 g of the expected compound are obtained.

D—1-(2-Amino-4-chlorophenyl)ethanone 2.55 ml of trifluoroacetic acid are added dropwise to a solution of 0.9 g of the compound from the preceding stage in 17 ml of DCM and the mixture is left stirring at AT overnight. The reaction mixture is washed with a 10% NaOH solution and with a saturated NaCl solution and dried over MgSO$_4$, and the solvent is evaporated. 0.5 g of the expected compound is obtained.

2. Preparations of the Compounds of Formula (VI)

Preparation 2.1

8-Methoxycinnolin-4(1H)-one $R_3$=8-OMe. (VI)

A mixture of 2.0 g of the compound from Preparation 1.1 in 8 ml of concentrated HCl is cooled to 0° C., a solution of 1.25 g of NaNO$_2$ in 2.7 ml of water is added dropwise while maintaining the temperature of the reaction mixture below 10° C. and the mixture is left stirring at 0° C. for 2 hours and at AT overnight. The reaction mixture is concentrated under vacuum, 50 ml of a sodium acetate solution are added and the precipitate formed is filtered off and washed with 20 ml of water. 1.95 g of the expected compound are obtained.

Preparation 2.2

7-Chlorocinnolin-4(1H)-one $R_3$=7—Cl. (VI)

A mixture of 2.2 g of the compound from Preparation 1.2 in 10 ml of concentrated HCl is cooled to 0° C., a solution of 1.34 g of NaNO$_2$ in 3 ml of water is added dropwise while maintaining the temperature of the reaction mixture below 10° C. and the mixture is left stirring at 0° C. for 2 hours and at AT overnight. The reaction mixture is concentrated under vacuum, a sodium acetate solution is added and the precipitate formed is filtered off and washed. 1.1 g of the expected compound are obtained.

3. Preparations of the Compounds of Formula (IV)

Preparation 3.1

3-Bromo-8-methoxycinnolin-4(1H)-one $R_3$=8-OMe; Hal=Br (IV)

1.4 g of potassium ethoxide are added to a mixture of 1.95 g of the compound from Preparation 2.1 in 20 ml of acetic acid and the combined mixture is heated to reflux. A solution of 0.68 ml of bromine in 2 ml of acetic acid is subsequently added dropwise and the mixture is heated at reflux for 1 hour 30 minutes. The acetic acid is concentrated under vacuum, the residue is taken up in water and the precipitate formed is filtered off, washed with water and dried. 2.8 g of the expected compound are obtained.

Preparation 3.2

3-Bromo-7-chlorocinnolin-4(1H)-one $R_3$=7-Cl; Hal=Br (IV)

0.63 g of potassium ethoxide is added to a mixture of 0.9 g of the compound from Preparation 2.2 in 8 ml of acetic acid and the combined mixture is heated to reflux. A solution of 0.38 ml of bromine in 2 ml of acetic acid is subsequently added dropwise and the mixture is heated at reflux for 3 hours. The acetic acid is concentrated under vacuum, the residue is taken up in water and the precipitate formed is filtered off and dried. 1.17 g of the expected compound are obtained.

4. Preparations of the Compounds of Formula (II)

Preparation 4.1

3-Bromo-1-(2,4-difluorobenzyl)-8-methoxycinnolin-4(1H)-one

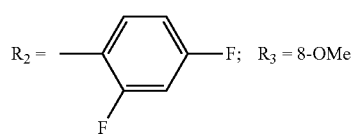

(II): $R_2$ = —F; $R_3$ = 8-OMe

A suspension of 0.35 g of NaH, at 60% in oil, in 15 ml of DMF is cooled to 0° C., a solution of 1.5 g of the compound from Preparation 3.1 in 15 ml of DMF is added dropwise, followed by a solution of 1.13 ml of 1-(bromomethyl)-2,4-difluorobenzene in 10 ml of DMF and the mixture is heated at 75° C. for 3 hours. After cooling to AT, the reaction mixture is run onto 100 ml of water, extraction is carried out twice with 80 ml of DCM, the organic phase is washed with a saturated NaCl solution and dried over MgSO$_4$, and the solvent is evaporated under vacuum. The residue is chromatographed on silica gel, elution being carried out with the gradient of the cyclohexane/AcOEt mixture from 80/20 (v/v) to 50/50 (v/v). 1.0 g of the expected compound is obtained.

Preparation 4.2

3-Bromo-7-chloro-1-(2,4-difluorobenzyl)cinnolin-4(1H)-one (II):

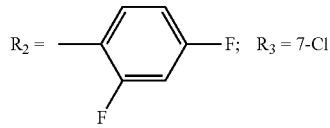

R$_2$ = ─⟨phenyl with F⟩─F; R$_3$ = 7-Cl

A suspension of 0.25 g of NaH, at 60% in oil, in 10 ml of DMF is cooled to 0° C., a solution of 1.1 g of the compound from Preparation 3.2 in 15 ml of DMF is added dropwise, followed by a solution of 0.82 ml of 1-(bromomethyl)-2,4-difluorobenzene in 5 ml of DMF, and the mixture is heated at 75° C. for 3 hours. After cooling to AT, the reaction mixture is run into water, extraction is carried out with DCM, the organic phase is washed with a saturated NaCl solution and dried over MgSO$_4$, and the solvent is evaporated under vacuum. The residue is chromatographed on silica gel, elution being carried out with the gradient of the cyclohexane/AcOEt mixture from 80/20 (v/v) to 50/50 (v/v). 1.2 g of the expected compound are obtained.

EXAMPLE 1

Compound No. 2

3-[2-Chloro-3-(trifluoromethyl)phenyl]-1-(2,4-difluorobenzyl)-8-methoxycinnolin-4(1H)-one 0.14 g of [2-chloro-3-(trifluoromethyl)phenyl]boronic acid and then 0.87 ml of a 2M Na$_2$CO$_3$ solution are added to a solution of 0.2 g of the compound from Preparation 4.1 in a mixture of 8 ml of toluene and 2 ml of MeOH. Nitrogen is sparged into the reaction mixture for 20 minutes, 0.12 g of tetrakis(triphenylphosphine)palladium is added and the mixture is heated at 80° C. for 18 hours. The reaction mixture is filtered through Célite® and washing is carried out with AcOEt. The filtrate is washed with 50 ml of 50% NaOH and with a saturated NaCl solution and dried over MgSO$_4$, and the solvents are evaporated under vacuum. The residue is chromatographed on silica gel, elution being carried out with the gradient of the cyclohexane/AcOEt mixture from 90/10 (v/v) to 70/30 (v/v). 0.2 g of the expected compound is obtained, M.p.=141-142° C.

$^1$H NMR: d$_6$-DMSO (250 MHz): δ (ppm): 3.84: s: 3H, 5.99: s: 2H, 6.96-7.22: m: 2H, 7.23-7.37: m: 1H, 7.41-7.57: m: 2H, 7.63-7.75: m: 1H, 7.78-7.90: m: 2H, 7.95-8.04: m: 1H.

EXAMPLE 2

Compound No. 76

7-Chloro-1-(2,4-difluorobenzyl)-3-[2-fluoro-3-(trifluoromethyl)phenyl]cinnolin-4(1H)-one 0.13 g of [2-fluoro-3-(trifluoromethyl)phenyl]boronic acid and then 0.86 ml of a 2M Na$_2$CO$_3$ solution are added to a solution of 0.2 g of the compound from Preparation 4.2 in a mixture of 8 ml of toluene and 2 ml of MeOH. Nitrogen is sparged into the reaction mixture for 20 minutes, 0.12 g of tetrakis(triphenylphosphine)palladium is added and the mixture is heated at 80° C. overnight. The reaction mixture is filtered through Célite® and the filtrate is concentrated under vacuum. The residue is extracted with AcOEt, the organic phase is washed with a 10% NaOH solution and with a saturated NaCl solution and dried over MgSO$_4$, and the solvents are evaporated under vacuum. The residue is chromatographed on silica gel, elution being carried out with the gradient of the cyclohexane/AcOEt mixture from 80/20 (v/v) to 60/40 (v/v). 0.16 g of the expected compound is obtained, M.p.=118-120° C.

$^1$H NMR: d$_6$-DMSO (250 MHz): δ (ppm): 5.83: s: 2H, 7.01-7.16: m: 1H, 7.27-7.65: m: 4H, 7.82-7.96: m: 2H, 8.08: d: 1H, 8.24: d: 1H.

The chemical structures and the physical properties of a few examples of compounds according to the invention, obtained by following the procedures described in the above Examples, are illustrated in the following table.

In this table:

Me represents a methyl group.

TABLE I

| Compound No. | R$_1$ | R$_2$ | R$_3$ | M.p. (° C.); MH$^+$; rt (min.) conditions |
|---|---|---|---|---|
| 1 | (2-F, 6-F phenyl with CF on ring) | (2,4-difluorophenyl) | 8-OMe | 116-118° C. 465; 10.59 A |

TABLE I-continued

| Compound No. | R₁ | R₂ | R₃ | M.p. (° C.); MH⁺; rt (min.) conditions |
|---|---|---|---|---|
| 2 | 2-Cl-3-Me-6-CF₃-phenyl | 2,4-difluoro-5-methylphenyl | 8-OMe | 141-142° C. 481; 11.1 A |
| 3 | 2-Cl-3-Me-6-CF₃-phenyl | 2,4-difluoro-5-methylphenyl | H | 168-170° C. 451; 10.62 A |
| 4 | 2,3-dichloro-6-methylphenyl | 2,4-difluoro-5-methylphenyl | 8-OMe | 103-105° C. 447; 10.94 A NMR |
| 5 | 2-F-3-Me-6-CF₃-phenyl | 2,4-difluorophenyl | H | 150-151° C. 435; 10.60 A |
| 6 | 2-F-3-methyl-6-CF₃-phenyl | 2,4-difluoro-5-methylphenyl | H | 435; 10.21 A |
| 7 | 2-F-3-Me-6-CF₃-phenyl | 2-F-4-Cl-5-methylphenyl | H | 172-174° C. 451; 11.07 A |
| 8 | 3-isopropyl-phenyl | 2,4-difluoro-5-methylphenyl | H | 390; 5.4 D |

TABLE I-continued

| Compound No. | R₁ | R₂ | R₃ | M.p. (° C.); MH⁺; rt (min.) conditions |
|---|---|---|---|---|
| 9 | 2-methyl-6-fluoro-3-(trifluoromethyl)phenyl | 2,4-difluorophenyl | 8-OMe | 135-136° C. 465; 10.63 A |
| 10 | 3-methyl-(trifluoromethoxy)phenyl | 2,4-difluorophenyl | 8-OMe | 153-155° C. 463; 11.66 A |
| 11 | 2,3-dichloro-6-methylphenyl | 3-fluoro-4-cyanophenyl | H | 272° C. 424; 9.90 A |
| 12 | 2-fluoro-3-methyl-6-(trifluoromethyl)phenyl | 3-fluoro-4-cyanophenyl | H | 220° C. 442; 10.05 A |
| 13 | 2-methoxy-4-fluoro-5-methylphenyl | 2,4-difluorophenyl | H | 148-150° C. 397; 9.66 A |
| 14 | 2,3-dichloro-6-methylphenyl | 2,5-difluorophenyl | H | 208-210° C. 417; 10.47 A |
| 15 | 2-methoxy-4-fluoro-3-methylphenyl | 2,4-difluorophenyl | H | 137-138° C. 397; 9.66 A |
| 16 | 2-methyl-6-methoxyphenyl | 2,4-difluorophenyl | H | 379; 434 D |

TABLE I-continued
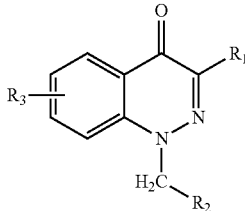
| Compound No. | R₁ | R₂ | R₃ | M.p. (° C.); MH⁺; rt (min.) conditions |
|---|---|---|---|---|
| 17 | 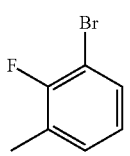 | 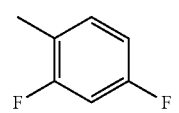 | H | 190-192° C. 445; 37.1 A |
| 18 | 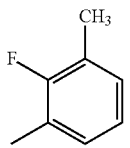 | 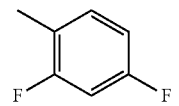 | H | 154-155° C. 381; 10.09 A |
| 19 | 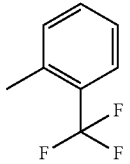 | 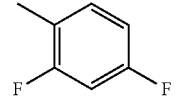 | H | 134-135° C. 417; 10.07 A |
| 20 | 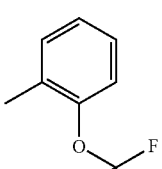 | 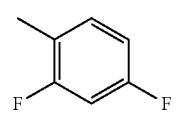 | H | 96-98° C. 433; 10.35 A |
| 21 | 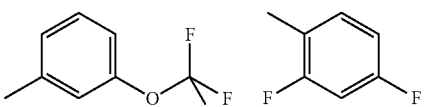 | 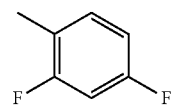 | H | 100-102° C. 433; 11.20 A |
| 22 | 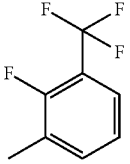 | 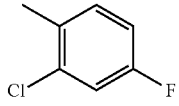 | H | 124-125° C. 451; 11.1 A |
| 23 | 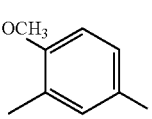 | 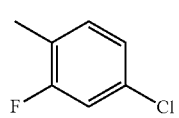 | H | 155-156° C. 413; 10.13 A |
| 24 | 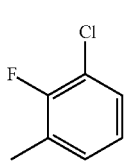 | 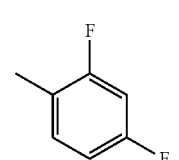 | H | 183-184° C. 401; 9.92 B |

TABLE I-continued
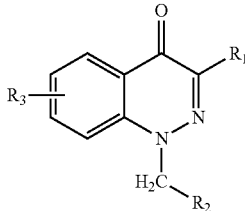
| Compound No. | R₁ | R₂ | R₃ | M.p. (° C.); MH⁺; rt (min.) conditions |
|---|---|---|---|---|
| 25 | 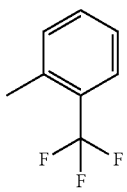 | 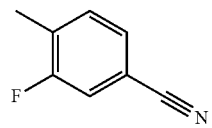 | H | 166-167° C. 424; 9.5 A |
| 26 | 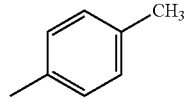 | 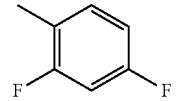 | H | 363; 4.95 D |
| 27 | 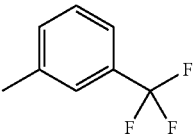 | 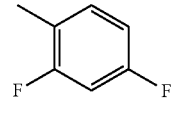 | H | 122-124° C. 417; 11.05 A |
| 28 | 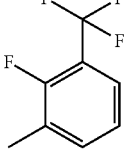 | 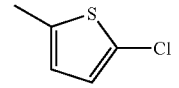 | H | 140° C. 439; 10.92 A |
| 29 | 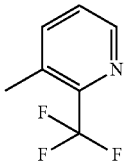 | 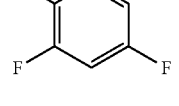 | H | 110-111° C. 418; 1.69 C |
| 30 | 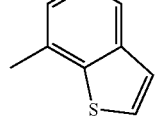 | 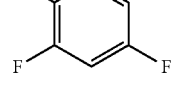 | H | 160-162° C. 405; 10.86 A |
| 31 | 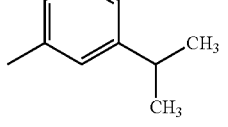 | 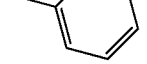 | H | 355; 4.94 D |
| 32 | 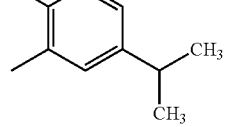 | 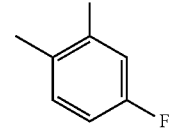 | H | 421; 4.77 D |

TABLE I-continued
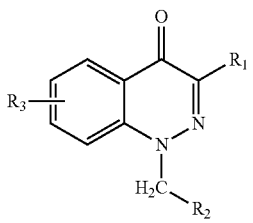
| Compound No. | R₁ | R₂ | R₃ | M.p. (° C.); MH⁺; rt (min.) conditions |
|---|---|---|---|---|
| 33 | 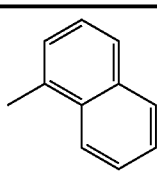 |  | H | 399; 4.83 D |
| 34 | 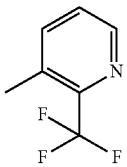 | 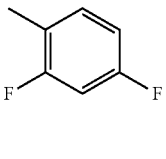 | H | 418; 1.69 C |
| 35 | 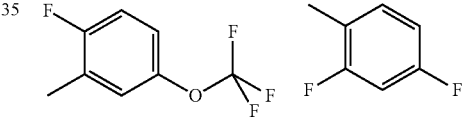 | 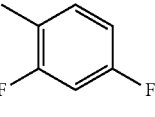 | H | 124-126° C. 451; 10.7 A |
| 36 | 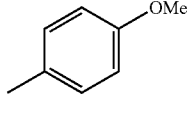 | 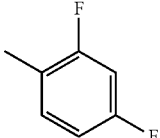 | H | 379; 4.61 D |
| 37 | 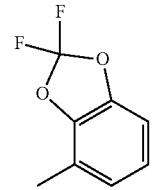 | 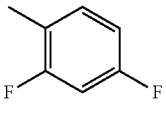 | H | 155-157° C. 429; 10.69 A |
| 38 | 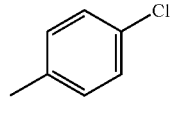 | 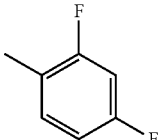 | H | 383; 5.15 D |
| 39 | 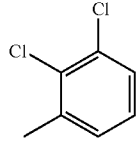 | 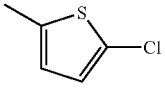 | H | 202-203° C. 421; 10.78 A |
| 40 |  | 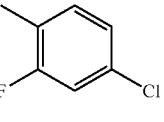 | H | 143-145° C. 433; 11.5 A |

TABLE I-continued
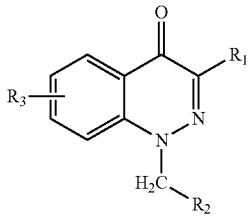
| Compound No. | R₁ | R₂ | R₃ | M.p. (° C.); MH⁺; rt (min.) conditions |
|---|---|---|---|---|
| 41 | 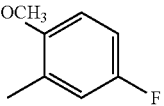 | 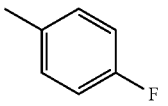 | H | 146-147° C. 379; 9.43 A |
| 42 | 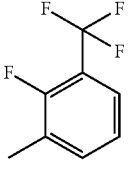 | 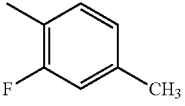 | H | 130-131° C. 431; 10.87 A |
| 43 | 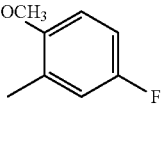 | 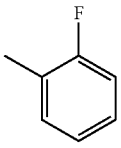 | H | 128-129° C. 379; 9.51 A |
| 44 | 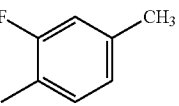 | 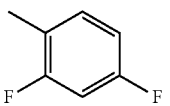 | H | 168-170° C. 381; 10.16 A |
| 45 | 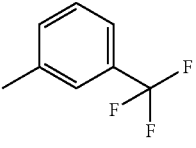 | 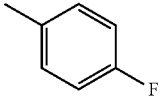 | H | 127-128° C. 399; 10.9 A |
| 46 | 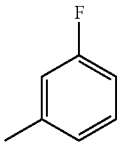 |  | H | 367; 4.9 D |
| 47 | 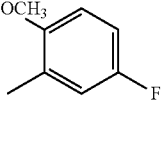 | 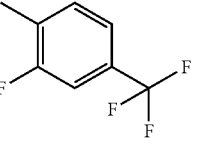 | H | 149-150° C. 447; 10.29 A |
| 48 | 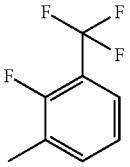 | 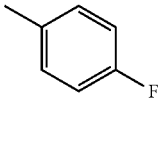 | H | 146-148° C. 417; 10.4 A |

TABLE I-continued
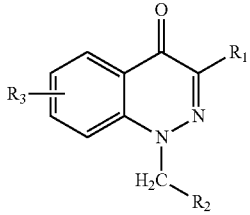
| Com-pound No. | R₁ | R₂ | R₃ | M.p. (° C.); MH⁺; rt (min.) conditions |
|---|---|---|---|---|
| 49 | 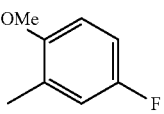 | 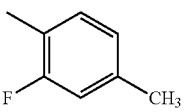 | H | 156-158° C. 393; 10.0 A |
| 50 | 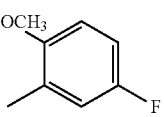 | 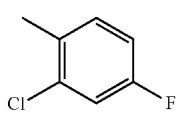 | H | 62-64° C. 413; 10.18 A |
| 51 | 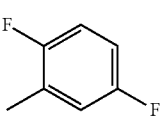 | 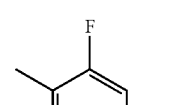 | H | 177-178° C. 385; 9.93 A |
| 52 | 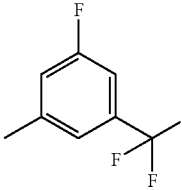 | 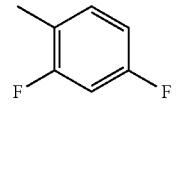 | H | 127-129° C. 435; 11.41 A |
| 53 | 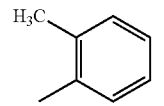 | 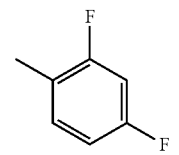 | H | 363; 4.51 D |
| 54 | 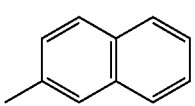 | 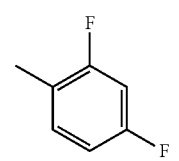 | H | 399; 5.24 D |
| 55 | 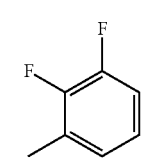 | 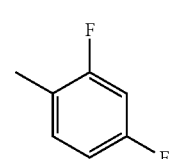 | H | 182-184° C. 385; 9.96 A |
| 56 | 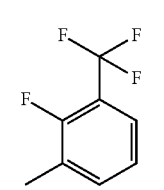 | 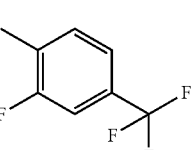 | H | 143-145° C. 485; 11.09 A |

TABLE I-continued

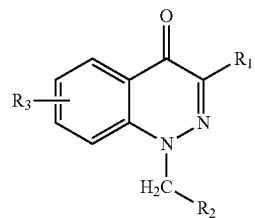

| Compound No. | R₁ | R₂ | R₃ | M.p. (° C.); MH⁺; rt (min.) conditions |
|---|---|---|---|---|
| 57 | 3-chloro-5-(trifluoromethyl)phenyl | 2,4-difluorophenyl | H | 164-166° C. 451; 19.17 A |
| 58 | 3,5-dichlorophenyl | 2,4-difluorophenyl | H | 198-200° C. 417; 11.37 Neutral B |
| 59 | 2-fluorophenyl | 2,4-difluorophenyl | H | 366; 33.5 A |
| 60 | 4-fluoro-2-methoxyphenyl | 2,4-dichlorophenyl | H | 70-72° C. 429; 10.77 A |
| 61 | 2-fluoro-3-(trifluoromethyl)phenyl | 5-(trifluoromethyl)pyridin-2-yl | H | 118° C. 468; 10.43 A |
| 62 | 4-tert-butyl-2-methoxyphenyl | 2,4-difluorophenyl | H | 72-74° C. 435; 10.92 A |
| 63 | 3-(trifluoromethyl)phenyl | 2-fluoro-4-(trifluoromethyl)phenyl | H | 158-159° C. 467; 11.55 A |

TABLE I-continued

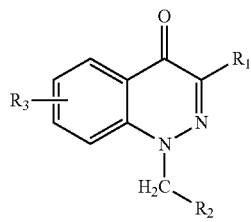

| Compound No. | R₁ | R₂ | R₃ | M.p. (° C.); MH⁺; rt (min.) conditions |
|---|---|---|---|---|
| 64 | 5-chloro-2-methyl-3-(trifluoromethyl)phenyl | 2,4-difluorophenyl | H | 117-118° C. 451; 10.78 A |
| 65 | 4-fluoro-2-methoxy-5-methylphenyl | 2,4-difluorophenyl | H | 134-136° C. 383; 10.09 A |
| 66 | phenyl | 2,4-difluorophenyl | H | 349; 4.78 D |
| 67 | 3-(trifluoromethyl)phenyl | 2,4-dichlorophenyl | H | 170-171° C. 449; 12.06 A |
| 68 | 3-(trifluoromethyl)phenyl | 2-chloro-4-fluorophenyl | H | 149-150° C. 433; 11.53 A |
| 69 | 3-(trifluoromethyl)phenyl | 2-fluoro-4,5-dimethylphenyl | H | 167-168° C. 413; 11.46 A |
| 70 | benzothiophen-2-yl | 4-chlorophenyl | H | 403; 5.75 D |
| 71 | 2-fluoro-3-(trifluoromethyl)phenyl | 2-fluorophenyl | H | 127-128° C. 417; 10.47 A |

TABLE I-continued
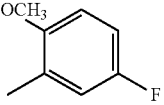
| Compound No. | R₁ | R₂ | R₃ | M.p. (° C.); MH⁺; rt (min.) conditions |
|---|---|---|---|---|
| 72 | 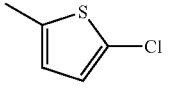 | 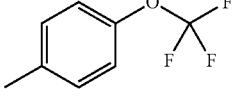 | H | 132-134° C. 401; 9.9 A |
| 73 | 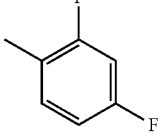 | 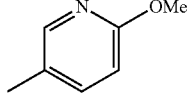 | H | 433; 5.37 D |
| 74 | 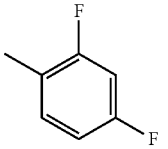 | 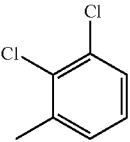 | H | 380; 4.24 D |
| 75 | 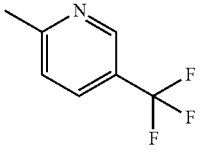 | 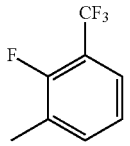 | H | 249° C. 450; 10.22 A |
| 76 | 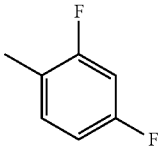 | 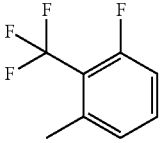 | 7-Cl | 118-120° C. 469; 2 C |
| 77 | 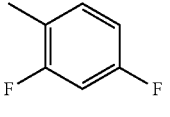 | 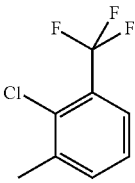 | 7-OMe | 177-178° C. 465; 1.78 A |
| 78 | 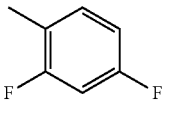 | 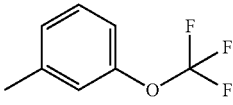 | 7-Cl | 196-198° C. 485; 2.01 A |
| 79 | 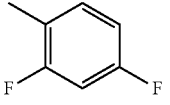 | | 7-OMe | 160-162° C. 463; 2.0 A |

TABLE I-continued

| Compound No. | R₁ | R₂ | R₃ | M.p. (° C.); MH⁺; rt (min.) conditions |
|---|---|---|---|---|
| 80 | 2-chloro-3-methyl-6-(trifluoromethyl)phenyl | 3-fluoro-4-cyanophenyl (via CH₂) | H | 231° C. 458; 9.59 A |
| 81 | 2-fluoro-3-methyl-6-(trifluoromethyl)phenyl | 2,4-difluorophenyl | 7-Cl | 160° C. 469; 1.97 A |
| 82 | 2,3-dichloro-6-methylphenyl (2-Cl, 3-Cl) | 2,4-difluorophenyl | 7-Cl | 212-214° C. 451; 2.04 A |
| 83 | 3-(trifluoromethoxy)phenyl | 2,4-difluorophenyl | 7-Cl | 137-138° C. 467; 11.3 A |
| 84 | 2-(methylsulfonyl)phenyl | 2,4-difluorophenyl | 7-Cl | 196-197° C. 461; 1.97 A |
| 85 | 2-fluoro-3-methyl-6-(trifluoromethyl)phenyl | 5-chloro-2-pyridyl | H | 172-173° C. 434; 1.76 A |
| 86 | 2-chloro-3-methyl-6-(trifluoromethyl)phenyl | 2,4-difluorophenyl | 6-Cl | 166-168° C. 485; 2.01 A |

TABLE I-continued

[Structure: quinazolinone-type core with R3 on benzene ring, R1 at 3-position, N-CH2-R2 at N1, carbonyl at 4-position]

| Compound No. | R₁ | R₂ | R₃ | M.p. (° C.); MH⁺; rt (min.) conditions |
|---|---|---|---|---|
| 87 | 2-fluoro-3-methyl-6-(trifluoromethyl)phenyl (F, CF₃ substituted phenyl with methyl) | 2,4-difluoro-3-methylphenyl | 6-Cl | 118-120° C. 469; 2.0 A |
| 88 | 2-fluoro-3-methyl-6-(trifluoromethyl)phenyl | 2,4-difluoro-3-methylphenyl | 6-OMe | 178-180° C. 465; 1.88 A |
| 89 | 2-fluoro-3-methyl-6-(trifluoromethyl)phenyl | 3,5-difluoro-2-methylpyridin-? | 6-Cl | 136° C. 470; 1.89 A |

Compound No. 4: $^1$H NMR (250 MHz, d$_6$-DMSO) δ ppm 3.84 (s, 3H), 5.98 (s, 2H), 6.96-7.21 (m, 2H), 7.23-7.36 (m, 1H), 7.41-7.56 (m, 4H), 7.73-7.85 (m, 2H).

The compounds according to the invention have shown a very good in vitro affinity (IC$_{50}$<500 nM) for human and rodent CB$_2$ receptors. Affinity binding tests were carried out according to the experimental conditions described by M. Rinaldi-Carmona in J. Pharmacol. Exp. Therap. 1998, 287, 644-650, with membranes resulting either from rodent tissues or from recombinant cell lines in which human CB$_2$ receptors were expressed (Munro et al., Nature 1993, 365, 61-65). The affinity of the compounds is expressed in the form of IC$_{50}$ (concentration causing 50% inhibition of the specific binding of the tritiated ligand used in vitro).

The compounds according to the invention have shown a modulatory effect on CB$_2$ receptors. In particular, the compounds according to the invention exhibit properties of agonist, inverse agonist and/or antagonist nature.

The agonist nature of the compounds according to the invention was demonstrated in the models of inhibition of adenylate cyclase (stimulated by forskolin) as described in M. Rinaldi-Carmona et al., J. Pharmacol. Exp. Ther. 1996, 278, 871-878, and 1998, 284, 644-650, and M Bouaboula et al., J. Biol Chem., 1997, 272, 22330-22339.

The antagonist nature of the compounds according to the invention was demonstrated in the models of reversion of the inhibition of adenylate cyclase (stimulated by forskolin) induced by an agonist of the CB$_2$ receptors as described in M. Rinaldi-Carmona et al., J. Pharmacol. Exp. Ther. 1996, 278, 871-878 and 1998, 284, 644-650.

The inverse agonist nature of the compounds according to the invention was demonstrated in the models of the activation of adenylate cyclase (stimulated by forskolin) as described in M. Portier et al., J. Pharmacol. Exp. Ther. 1999, 288, 582-589.

The compounds according to the invention also have a good in vivo affinity for the CB$_2$ receptors present in the mouse spleen when they are administered orally. The tests were carried out according to the experimental conditions described by Rinaldi-Carmona et al., J. Pharmacol. Exp. Ther., 1998, 284, 644-650. The affinity of the compounds is expressed in the form of ED$_{50}$ (dose causing 50% inhibition of the specific binding of the tritiated ligand used ex vivo).

The compounds of the present invention are in particular active principles compatible with their use as medicaments and/or pharmaceutical compositions.

According to one of its aspects, the present invention relates to the use of a compound of formula (I) or of one of its pharmaceutically acceptable salts in the preparation of medicaments intended to prevent or treat any human pathology and/or for veterinary use. Thus, the compounds according to the invention can be used in man or in animals (in particular in mammals, including, without implied limitation, dogs, cats, horses, cattle or sheep) for the prevention or treatment of diseases involving CB$_2$ receptors.

Mention may be made, for example, of the following diseases or conditions:

disorders of the immune system: in particular autoimmune diseases, nonexhaustively including: psoriasis, lupus erythematosus, diseases of the connective tissue, Sjögren's syndrome, ankylosing spondylarthritis, rheumatoid arthritis, rectional arthritis, undifferentiated spondylarthritis, Charcot's disease, Behcet's disease, autoimmune haemolytic anaemias, multiple sclerosis, amyotropic lateral sclerosis, amyloidosis, graft rejection and diseases affecting the plasma cell line;

allergic diseases: in particular delayed or immediate hypersensitivity, asthma, allergic rhinitis, contact dermatitis and allergic conjunctivitis;

infectious parasitic, viral or bacterial diseases, including in particular AIDS and meningitis;

amyloidosis and diseases affecting the line of the lympho-haematopoietic system;

chronic liver diseases of alcoholic origin, cirrhosis, chronic liver diseases of viral and toxic origin, and also steatohepatitis of non-alcoholic origin and primary liver cancer;

inflammatory diseases: in particular diseases of the joints: arthritis, rheumatoid arthritis, osteoarthritis, spondylitis, gout, vasculitis, Crohn's disease, inflammatory bowel disease (IBD) or irritable bowel syndrome (IBS), and ulcerative colitis acute pancreatitis;

bone diseases and osteoporosis;

pain: in particular chronic pain of inflammatory type, neuropathic pain and acute peripheral pain;

eye conditions: in particular ocular hypertension and glaucoma;

pulmonary conditions: diseases of the respiratory tract, asthma, chronic bronchitis, chronic obstructive pulmonary disease (COPD) or emphysema;

diseases of the central nervous system and neurodegenerative diseases: in particular Tourette's syndrome, Parkinson's disease, Alzheimer's disease, senile dementia, chorea, Huntington's chorea, epilepsy, psychoses, depression and spinal cord lesions.

The compound of formula (I) according to the invention can be used as medicament for the treatment or prevention of:

migraine, stress, diseases of psychosomatic origin, outbursts of panic (panic attack or acute anxiety attack), epilepsy, movement disorders, dizziness, vomiting or nausea, in particular resulting from a chemotherapy;

cardiovascular diseases, in particular hypertension, arteriosclerosis, heart attack or cardiac ischaemia;

renal ischaemia;

cancers: in particular benign skin tumours, cancerous tumours and papillomas, prostate tumours, brain tumours (examples: glioblastomas, medulloepitheliomas, medulloblastomas, neuroblastomas, tumours of embryonic origin, astrocytomas, astroblastomas, ependymomas, oligodendrogliomas, plexus tumours, neuro-epitheliomas, tumour of the epiphysis, ependymoblastomas, neuroectodermal tumour, malignant meningiomas, sarcomatoses, malignant melanomas or schwannomas);

gastrointestinal disorders, diarrhoea, ulcers, bladder and urinary disorders, nephritis, disorders of endocrine origin, haemorrhagic shock, septic shock, Raynaud's syndrome and fertility disorders;

obesity, type II diabetes, metabolic syndrome, insulin resistance and adipose tissue inflammation.

More particularly, the compounds of formula (I) according to the present invention will be of use in the preparation of medicaments which make possible the prevention and/or treatment of pain, inflammatory diseases, autoimmune diseases, allergic diseases, infectious diseases, neurodegenerative diseases, cardiovascular diseases, cancers, gastrointestinal diseases, obesity, type II diabetes, insulin resistance and adipose tissue inflammation.

The use of the compounds according to the invention for the prevention and/or treatment of the abovementioned diseases and in the preparation of medicaments intended to treat these diseases forms an integral part of the invention.

The compounds of formula (I) above, or one of their pharmaceutically acceptable salts, can be used at daily doses of 0.01 to 100 mg per kilo of body weight of the mammal to be treated, preferably at daily doses of 0.1 to 50 mg/kg. In man, the dose can preferably vary from 0.1 to 4000 mg per day, more particularly from 0.5 to 1000 mg, depending on the age of the subject to be treated or the type of treatment, prophylactic or curative.

Thus, according to another of its aspects, the present invention relates to pharmaceutical compositions including, as active principle, a compound of formula (I) or one of its pharmaceutically acceptable salts and also one or more pharmaceutically acceptable excipients.

In the pharmaceutical compositions of the present invention for oral, sublingual, inhaled, subcutaneous, intramuscular, intravenous, topical, local, intratracheal, intranasal, transdermal or rectal administration, the active principles can be administered in unit administration forms, as a mixture with conventional pharmaceutical vehicles, to animals and to human beings.

The appropriate unit administration forms comprise oral forms, such as tablets, soft or hard gelatin capsules, powders, granules, oral solutions or suspensions, sublingual, buccal, intratracheal, intraocular, intranasal or inhalatory administration forms, aerosols, topical or transdermal administration forms, implants, subcutaneous, intramuscular or intravenous administration forms and rectal administration forms.

For topical administration, the compounds according to the invention can be used in creams, ointments, gels or lotions.

By way of example, a unit administration form of a compound according to the invention in the tablet form can comprise the following components:

Compound according to the invention: 50.0 mg
Mannitol: 223.75 mg
Sodium croscarmellose: 6.0 mg
Maize starch: 15.0 mg
Hydroxypropylmethylcellulose: 2.25 mg
Magnesium stearate: 3.0 mg Orally, the dose of active principle administered per day can reach 0.01 to 100 mg/kg, taken all at once or at intervals throughout the day, preferably 0.02 to 50 mg/kg.

There may be particular cases where higher or lower dosages are appropriate; such dosages do not depart from the scope of the invention. According to the normal practice, the dosage appropriate to each patient is determined by the physician according to the method of administration and the weight and the response of the said patient.

According to another of its aspects, the present invention also relates to a method for the treatment of the pathologies indicated above which comprises the administration, to a patient, of an effective dose of a compound according to the invention or of one of its pharmaceutically acceptable salts.

The compounds according to the invention can also be used in the preparation of compositions for veterinary use.

Furthermore, the compounds according to the invention, as are or in the radiolabelled form, can be used as pharmacological tools in man or in animals for the detection and the labelling of $CB_2$ cannabinoid receptors.

We claim:

1. A compound of formula (I):

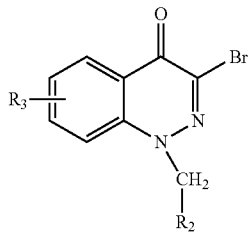

wherein:
R₁ represents:
- a phenyl which is unsubstituted or substituted one or more times by substituents chosen independently from a halogen atom, an Alk group, an OAlk group, a cyano, an —NH SO₂Alk group and an —SO₂Alk group;
- a naphthyl which is unsubstituted or substituted one or more times by substituents chosen independently from a halogen atom, an Alk group and an OAlk group;
- a pyridyl which is unsubstituted or substituted one or more times by substituents chosen independently from a halogen atom, an Alk group and an OAlk group;
- a 1-benzothienyl which is unsubstituted or substituted one or more times by substituents chosen independently from a halogen atom, an Alk group and an OAlk group; or
- a 1,3-benzodioxolyl which is unsubstituted or substituted one or more times by substituents chosen independently from a halogen atom, an Alk group and an OAlk group;

R₂ represents:
- a phenyl which is unsubstituted or substituted once or twice by substituents chosen independently from a halogen atom, an Alk group and a cyano; or
- a thienyl or a pyridyl, each of which is substituted by a halogen atom or an Alk group;

R₃ represents a hydrogen atom, a halogen atom, an Alk group or an OAlk group; and Alk represents a (C₁-C₄)alkyl which is unsubstituted or substituted one or more times by a fluorine atom;

or an acid addition salt thereof.

2. The compound according to claim 1, wherein:
R₁ represents:
- a phenyl which is unsubstituted or substituted once or twice by substituents chosen independently from a halogen atom, an Alk group, an OAlk group and an —SO₂Alk group;
- a naphthyl;
- a pyridyl substituted by an Alk group or an OAlk group;
- a 1-benzothienyl; or
- a 1,3-benzodioxolyl substituted by one or more fluorine atoms; and R₃ represents a hydrogen or halogen atom or an OAlk group;

or an acid addition salt thereof.

3. The compound according to claim 1, wherein:
R₁ represents:
- a phenyl, a 4-chlorophenyl, a 2-fluorophenyl, a 3-fluorophenyl, a 2-methylphenyl, a 4-methylphenyl, a 3-isopropylphenyl, a 2-trifluoromethylphenyl, a 3-trifluoromethylphenyl, a 2-methoxyphenyl, a 4-methoxyphenyl, a 2-trifluoromethoxyphenyl, a 3-trifluoromethoxyphenyl, a 4-trifluoromethoxyphenyl, a 2,3-dichlorophenyl, a 3,5-dichlorophenyl, a 2,3-difluorophenyl, a 2,5-difluorophenyl, a 3-chloro-2-fluorophenyl, a 2-chloro-3-trifluoromethylphenyl, a 3-chloro-5-trifluoromethylphenyl, a 4-chloro-2-trifluoromethylphenyl, a 3-bromo-2-fluorophenyl, a 2-fluoro-3-methylphenyl, a 2-fluoro-4-methylphenyl, a 2-fluoro-3-trifluoromethylphenyl, a 3-fluoro-2-trifluoromethylphenyl, a 3-fluoro-5-trifluoromethylphenyl, a 3-fluoro-2-methoxyphenyl, a 4-fluoro-2-methoxyphenyl, a 2-fluoro-5-trifluoromethoxyphenyl, a 3-isopropyl-6-methoxyphenyl, a 3-(tert-butyl)-6-methoxyphenyl, a 2-(methylsulphonyl)phenyl;
- a naphthyl;
- a 2-methoxypyrid-5-yl, a 2-trifluoromethylpyrid-3-yl;
- a benzothien-2-yl, a benzothien-7-yl; or
- a 2,2-difluorobenzodioxol-4-yl;

R₂ represents:
- a phenyl, a 4-chlorophenyl, a 2-fluorophenyl, a 4-fluorophenyl, a 2,4-dichlorophenyl, a 2,4-difluorophenyl, a 2-chloro-4-fluorophenyl, a 4-chloro-2-fluorophenyl, a 2-fluoro-4-methylphenyl, a 2-fluoro-4-trifluoromethylphenyl or a 2-fluoro-4-cyanophenyl;
- a 2-chlorothien-5-yl, a 3-trifluoromethylpyrid-6-yl, a 5-chloropyrid-2-yl or a 3,5-difluoropyrid-2-yl; and R₃ represents a hydrogen atom, a chlorine atom or a methoxy;

or an acid addition salt thereof.

4. The compound according to claim 1, which is:
1-(2,4-difluorobenzyl)-3-[2-fluoro-3-(trifluoromethyl)phenyl]-8-methoxycinnolin-4(1H)-one;
3-[2-chloro-3-(trifluoromethyl)phenyl]-1-(2,4-difluorobenzyl)-8-methoxycinnolin-4(1H)-one;
3-[2-chloro-3-(trifluoromethyl)phenyl]-1-(2,4-difluorobenzyl)cinnolin-4(1H)-one;
3-(2,3-dichlorophenyl)-1-(2,4-difluorobenzyl)-8-methoxycinnolin-4(1H)-one;
1-(2,4-difluorobenzyl)-3-[2-fluoro-3-(trifluoromethyl)phenyl]cinnolin-4(1H)-one;
1-(2,4-difluorobenzyl)-3-[3-fluoro-2-(trifluoromethyl)phenyl]cinnolin-4(1H)-one;
1-(4-chloro-2-fluorobenzyl)-3-[2-fluoro-3-(trifluoromethyl)phenyl]cinnolin-4(1H)-one;
1-(2,4-difluorobenzyl)-3-(3-isopropylphenyl)cinnolin-4(1H)-one;
1-(2,4-difluorobenzyl)-3-[3-fluoro-2-(trifluoromethyl)phenyl]-8-methoxycinnolin-4(1H)-one;
1-(2,4-difluorobenzyl)-8-methoxy-3-[3-(trifluoromethoxy)phenyl]cinnolin-4(1H)-one;
4-{[3-(2,3-dichlorophenyl)-4-oxocinnolin-1(4H)-yl]methyl}-3-fluorobenzonitrile;
3-fluoro-4-({3-[2-fluoro-3-(trifluoromethyl)phenyl]-4-oxocinnolin-1 (4H)-yl}methyl)benzonitrile;
1-(2,4-difluorobenzyl)-3-(4-fluoro-2-methoxyphenyl)cinnolin-4(1H)-one;
3-(2,3-dichlorophenyl)-1-(2,4-difluorobenzyl)cinnolin-4(1H)-one;
1-(2,4-difluorobenzyl)-3-(5-fluoro-2-methoxyphenyl)cinnolin-4(1H)-one;
1-(2,4-difluorobenzyl)-3-(2-methoxyphenyl)cinnolin-4(1H)-one;
3-(3-bromo-2-fluorophenyl)-1-(2,4-difluorobenzyl)cinnolin-4(1H)-one;

1-(2,4-difluorobenzyl)-3-(2-fluoro-3-methylphenyl)cinnolin-4(1H)-one;
1-(2,4-difluorobenzyl)-3-[2-(trifluoromethyl)phenyl]cinnolin-4(1H)-one;
1-(2,4-difluorobenzyl)-3-[2-(trifluoromethoxy)phenyl]cinnolin-4(1H)-one;
1-(2,4-difluorobenzyl)-3-[3-(trifluoromethoxy)phenyl]cinnolin-4(1H)-one;
1-(2-chloro-4-fluorobenzyl)-3-[2-fluoro-3-(trifluoromethyl)phenyl]cinnolin-4(1H)-one;
1-(4-chloro-2-fluorobenzyl)-3-(5-fluoro-2-methoxyphenyl)cinnolin-4(1H)-one;
3-(3-chloro-2-fluorophenyl)-1-(2,4-difluorobenzyl)cinnolin-4(1H)-one;
3-fluoro-4-({4-oxo-3-[2-(trifluoromethyl)phenyl]cinnolin-1(4H)-yl}methyl)benzonitrile;
1-(2,4-difluorobenzyl)-3-(4-methylphenyl)cinnolin-4(1H)-one;
1-(2,4-difluorobenzyl)-3-[3-(trifluoromethyl)phenyl]cinnolin-4(1H)-one;
1-[(5-chlorothien-2-yl)methyl]-3-[2-fluoro-3-(trifluoromethyl)phenyl]cinnolin-4(1H)-one;
1-(2,4-difluorobenzyl)-3-[2-(trifluoromethyl)pyridin-3-yl]cinnolin-4(1H)-one;
3-(1-benzothien-7-yl)-1-(2,4-difluorobenzyl)cinnolin-4(1H)-one;
1-benzyl-3-(3-isopropylphenyl)cinnolin-4(1H)-one;
1-(2,4-difluorobenzyl)-3-(5-isopropyl-2-methoxyphenyl)cinnolin-4(1H)-one;
1-(2,4-difluorobenzyl)-3-(1-naphthyl)cinnolin-4(1H)-one;
1-(2,4-difluorobenzyl)-3-[2-(trifluoromethyl)pyridin-3-yl]cinnolin-4(1H)-one;
1-(2,4-difluorobenzyl)-3-[2-fluoro-5-(trifluoromethoxy)phenyl]cinnolin-4(1H)-one;
1-(2,4-difluorobenzyl)-3-(4-methoxyphenyl)cinnolin-4(1H)-one;
3-(2,2-difluoro-1,3-benzodioxol-4-yl)-1-(2,4-difluorobenzyl)cinnolin-4(1H)-one;
3-(4-chlorophenyl)-1-(2,4-difluorobenzyl)cinnolin-4(1H)-one;
1-[(5-chlorothien-2-yl)methyl]-3-(2,3-dichlorophenyl)cinnolin-4(1H)-one;
1-(4-chloro-2-fluorobenzyl)-3-[3-(trifluoromethyl)phenyl]cinnolin-4(1H)-one;
1-(4-fluorobenzyl)-3-(5-fluoro-2-methoxyphenyl)cinnolin-4(1H)-one;
1-(2-fluoro-4-methylbenzyl)-3-[2-fluoro-3-(trifluoromethyl)phenyl]cinnolin-4(1H)-one;
1-(2-fluorobenzyl)-3-(5-fluoro-2-methoxyphenyl)cinnolin-4(1H)-one;
1-(2,4-difluorobenzyl)-3-(2-fluoro-4-methylphenyl)cinnolin-4(1H)-one;
1-(4-fluorobenzyl)-3-[3-(trifluoromethyl)phenyl]cinnolin-4(1H)-one;
1-(2,4-difluorobenzyl)-3-(3-fluorophenyl)cinnolin-4(1H)-one;
3-(5-fluoro-2-methoxyphenyl)-1-[2-fluoro-4-(trifluoromethyl)benzyl]cinnolin-4(1H)-one;
1-(4-fluorobenzyl)-3-[2-fluoro-3-(trifluoromethyl)phenyl]cinnolin-4(1H)-one;
3-(5-fluoro-2-methoxyphenyl)-1-(2-fluoro-4-methylbenzyl)cinnolin-4(1H)-one;
1-(2-chloro-4-fluorobenzyl)-3-(5-fluoro-2-methoxyphenyl)cinnolin-4(1H)-one;
1-(2,4-difluorobenzyl)-3-(2,5-difluorophenyl)cinnolin-4(1H)-one;
1-(2,4-difluorobenzyl)-3-[3-fluoro-5-(trifluoromethyl)phenyl]cinnolin-4(1H)-one;
1-(2,4-difluorobenzyl)-3-(2-methylphenyl)cinnolin-4(1H)-one;
1-(2,4-difluorobenzyl)-3-(2-naphthyl)cinnolin-4(1H)-one;
1-(2,4-difluorobenzyl)-3-(2,3-difluorophenyl)cinnolin-4(1H)-one;
1-[2-fluoro-4-(trifluoromethyl)benzyl]-3-[2-fluoro-3-(trifluoromethyl)phenyl]cinnolin-4(1H)-one;
3-[3-chloro-5-(trifluoromethyl)phenyl]-1-(2,4-difluorobenzyl)cinnolin-4(1H)-one;
3-(3,5-dichlorophenyl)-1-(2,4-difluorobenzyl)cinnolin-4(1H)-one;
1-(2,4-difluorobenzyl)-3-(2-fluorophenyl)cinnolin-4(1H)-one;
1-(2,4-dichlorobenzyl)-3-(5-fluoro-2-methoxyphenyl)cinnolin-4(1H)-one;
3-[2-fluoro-3-(trifluoromethyl)phenyl]-1-{[5-(trifluoromethyl)pyridin-2-yl]methyl}cinnolin-4(1H)-one;
3-(5-(tert-butyl)-2-methoxyphenyl)-1-(2,4-difluorobenzyl)cinnolin-4(1H)-one;
1-[2-fluoro-4-(trifluoromethyl)benzyl]-3-[3-(trifluoromethyl)phenyl]cinnolin-4(1H)-one;
3-[4-chloro-2-(trifluoromethyl)phenyl]-1-(2,4-difluorobenzyl)cinnolin-4(1H)-one;
1-(2,4-difluorobenzyl)-3-(5-fluoro-2-hydroxyphenyl)cinnolin-4(1H)-one;
1-(2,4-difluorobenzyl)-3-phenylcinnolin-4(1H)-one;
1-(2,4-dichlorobenzyl)-3-[3-(trifluoromethyl)phenyl]cinnolin-4(1H)-one;
1-(2-chloro-4-fluorobenzyl)-3-[3-(trifluoromethyl)phenyl]cinnolin-4(1H)-one;
1-(2-fluoro-4-methylbenzyl)-3-[3-(trifluoromethyl)phenyl]cinnolin-4(1H)-one;
3-(1-benzothien-2-yl)-1-(4-chlorobenzyl)cinnolin-4(1H)-one;
1-(2-fluorobenzyl)-3-[2-fluoro-3-(trifluoromethyl)phenyl]cinnolin-4(1H)-one;
1-[(5-chlorothien-2-yl)methyl]-3-(5-fluoro-2-methoxyphenyl)cinnolin-4(1H)-one;
1-(2,4-difluorobenzyl)-3-[4-(trifluoromethoxy)phenyl]cinnolin-4(1H)-one;
1-(2,4-difluorobenzyl)-3-(6-methoxypyridin-3-yl)cinnolin-4(1H)-one;
3-(2,3-dichlorophenyl)-1-{[5-(trifluoromethyl)pyridin-2-yl]methyl}cinnolin-4(1H)-one;
7-chloro-1-(2,4-difluorobenzyl)-3-[2-fluoro-3-(trifluoromethyl)phenyl]cinnolin-4(1H)-one;
1-(2,4-difluorobenzyl)-3-[3-fluoro-2-(trifluoromethyl)phenyl]-7-methoxycinnolin-4(1H)-one;
7-chloro-3-[2-chloro-3-(trifluoromethyl)phenyl]-1-(2,4-difluorobenzyl)cinnolin-4(1H)-one;
1-(2,4-difluorobenzyl)-7-methoxy-3-[3-(trifluoromethoxy)phenyl]cinnolin-4(1H)-one;
4-({3-[2-chloro-3-(trifluoromethyl)phenyl]-4-oxocinnolin-1(4H)-yl}methyl)-3-fluorobenzonitrile;
7-chloro-1-(2,4-difluorobenzyl)-3-[3-fluoro-2-(trifluoromethyl)phenyl]cinnolin-4(1H)-one;
7-chloro-3-(2,3-dichlorophenyl)-1-(2,4-difluorobenzyl)cinnolin-4(1H)-one;
7-chloro-1-(2,4-difluorobenzyl)-3-[3-(trifluoromethoxy)phenyl]cinnolin-4(1H)-one;
7-chloro-1-(2,4-difluorobenzyl)-3-[2-(methylsulphonyl)phenyl]cinnolin-4(1H)-one;
1-[(5-chloropyridin-2-yl)methyl]-3-[2-fluoro-3-(trifluoromethyl)phenyl]cinnolin-4(1H)-one;

6-chloro-3-[2-chloro-3-(trifluoromethyl)phenyl]-1-(2,4-difluorobenzyl)cinnolin-4(1H)-one;

6-chloro-1-(2,4-difluorobenzyl)-3-[2-fluoro-3-(trifluoromethyl)phenyl]cinnolin-4(1H)-one;

1-(2,4-difluorobenzyl)-3-[2-fluoro-3-(trifluoromethyl)phenyl]-6-methoxycinnolin-4(1H)-one; or 6-chloro-1-[(3,5-difluoropyridin-2-yl)methyl]-3-[2-fluoro-3-(trifluoromethyl)phenyl]cinnolin-4(1H)-one;

or an acid addition salt thereof.

5. A pharmacetucial composition comprising the compound according to claim 1, or an acid addition salt thereof, and at least one pharmaceutically acceptable excipient.

6. A pharmacetucial composition comprising the compound according to claim 2, or an acid addition salt thereof, and at least one pharmaceutically acceptable excipient.

7. A pharmacetucial composition comprising the compound according to claim 3, or an acid addition salt thereof, and at least one pharmaceutically acceptable excipient.

8. A pharmacetucial composition comprising the compound according to claim 4, or an acid addition salt thereof, and at least one pharmaceutically acceptable excipient.

9. A process for preparing the compound of formula (I) according to claim 1, comprising:
reacting a compound of formula:

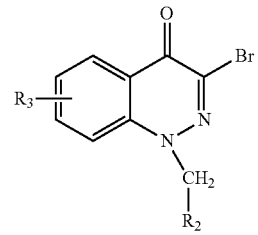

(II)

wherein $R_2$ and $R_3$ are as defined in claim 1, in the presence of a base, with a compound of formula (III):

$$R_1\text{—B(OH)}_2 \quad\quad\quad (III)$$

wherein $R_1$ is as defined in claim 1.

* * * * *